(12) United States Patent
Sherwood et al.

(10) Patent No.: US 7,456,077 B2
(45) Date of Patent: *Nov. 25, 2008

(54) METHOD FOR INTERCONNECTING ANODES AND CATHODES IN A FLAT CAPACITOR

(75) Inventors: Gregory J. Sherwood, North Oaks, MN (US); Brian L. Schmidt, White Bear Lake, MN (US); James M. Poplett, Plymouth, MN (US); Brian V. Waytashek, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 380 days.

This patent is subject to a terminal disclaimer.

(21) Appl. No.: 10/874,798

(22) Filed: Jun. 23, 2004

(65) Prior Publication Data

US 2005/0017888 A1    Jan. 27, 2005

Related U.S. Application Data

(60) Continuation-in-part of application No. 10/804,288, filed on Mar. 18, 2004, now Pat. No. 6,999,304, which is a division of application No. 10/299,234, filed on Nov. 19, 2002, now Pat. No. 6,709,946, which is a division of application No. 09/706,519, filed on Nov. 3, 2000, now Pat. No. 6,509,588.

(51) Int. Cl.
*H01L 21/00* (2006.01)

(52) U.S. Cl. ................ 438/396; 438/395; 438/397

(58) Field of Classification Search .......... 438/395–397
See application file for complete search history.

(56) References Cited

U.S. PATENT DOCUMENTS

| 1,474,486 A | 11/1923 | Macpherson |
| 1,931,043 A | 10/1933 | Taylor |
| 2,555,326 A | 6/1951 | Doughty, Jr. |

(Continued)

FOREIGN PATENT DOCUMENTS

EP    0224733 A1    6/1987

(Continued)

OTHER PUBLICATIONS

"International Search Report and Written Opinion for Application No. PCT/US2005/021898, date mailed Nov. 3, 2005", 14 pgs.

(Continued)

*Primary Examiner*—Laura M Schillinger
(74) *Attorney, Agent, or Firm*—Schwegman, Lundberg & Woessner, P.A.

(57) ABSTRACT

A method includes connecting together one or more anode connection members of one or more anode foils and one or more cathode connection members of one or more cathode foils and electrically isolating the one or more anode foils from the one or more cathode foils. A capacitor stack includes a plurality of cathode layers having cathode connection members and a plurality of anode layers having anode connection members. The anode connection members are connected to the cathode connection members and configured such that the anode layers can be electrically separated from the cathode layers by cutting only the anode connection members or the cathode connection members.

13 Claims, 11 Drawing Sheets

US 7,456,077 B2

Page 2

U.S. PATENT DOCUMENTS

| | | | |
|---|---|---|---|
| 3,150,301 A | 9/1964 | Schils et al. | |
| 3,389,311 A | 6/1968 | Rayno | |
| 3,424,857 A | 1/1969 | Miller et al. | |
| 3,643,168 A | 2/1972 | Manicki | 325/459 |
| 3,686,535 A | 8/1972 | Piper | |
| 3,686,538 A | 8/1972 | Webster | |
| 3,723,926 A | 3/1973 | Thomas et al. | 335/268 |
| 3,777,570 A | 12/1973 | Thomas et al. | 73/398 |
| 3,803,457 A | 4/1974 | Yamamoto | |
| 3,818,177 A | 6/1974 | Needham et al. | |
| 3,826,143 A | 7/1974 | Thomas et al. | 73/398 C |
| 3,828,227 A | 8/1974 | Millard et al. | 317/230 |
| 3,859,574 A | 1/1975 | Brazier | 317/230 |
| 3,894,210 A | 7/1975 | Smith et al. | |
| 3,938,228 A | 2/1976 | Kemkers et al. | 29/25.42 |
| 4,033,848 A | 7/1977 | Strempel et al. | |
| 4,045,644 A | 8/1977 | Shafer et al. | |
| 4,047,790 A | 9/1977 | Carino | 439/720 |
| 4,059,216 A | 11/1977 | Meyer | |
| 4,086,148 A | 4/1978 | Badia | 204/33 |
| 4,088,108 A | 5/1978 | Hager | 123/148 CC |
| 4,107,022 A | 8/1978 | Strempel et al. | |
| 4,113,921 A | 9/1978 | Goldstein et al. | |
| 4,131,935 A | 12/1978 | Clement | 361/433 |
| 4,171,477 A | 10/1979 | Funari | |
| 4,247,883 A | 1/1981 | Thompson et al. | |
| 4,267,565 A | 5/1981 | Puppolo et al. | |
| 4,307,142 A | 12/1981 | Blitstein et al. | |
| 4,384,188 A | 5/1983 | Wright, Jr. | |
| 4,394,713 A | 7/1983 | Yoshida | |
| 4,481,083 A | 11/1984 | Ball et al. | 204/38 A |
| 4,562,511 A | 12/1985 | Nishino et al. | |
| 4,571,662 A | 2/1986 | Conquest et al. | 361/306 |
| 4,782,340 A | 11/1988 | Czubatyj et al. | 340/825.83 |
| 4,931,899 A | 6/1990 | Pruett | |
| 5,041,942 A | 8/1991 | Carrico | |
| 5,131,388 A * | 7/1992 | Pless et al. | 607/5 |
| 5,302,414 A | 4/1994 | Alkhimov et al. | |
| 5,333,095 A | 7/1994 | Stevenson et al. | |
| 5,377,073 A | 12/1994 | Fukaumi et al. | |
| 5,439,760 A * | 8/1995 | Howard et al. | 429/94 |
| 5,471,087 A | 11/1995 | Buerger, Jr. | 257/532 |
| 5,507,966 A * | 4/1996 | Liu | 252/62.2 |
| 5,522,851 A * | 6/1996 | Fayram | 607/5 |
| 5,527,346 A | 6/1996 | Kroll | 607/5 |
| 5,554,178 A | 9/1996 | Dahl et al. | 607/122 |
| 5,584,890 A * | 12/1996 | MacFarlane et al. | 29/25.03 |
| 5,628,801 A * | 5/1997 | MacFarlane et al. | 29/25.03 |
| 5,634,938 A | 6/1997 | Swanson et al. | |
| 5,658,319 A | 8/1997 | Kroll | 607/7 |
| 5,660,737 A * | 8/1997 | Elias et al. | 216/6 |
| 5,716,729 A * | 2/1998 | Sunderland et al. | 429/66 |
| 5,754,394 A * | 5/1998 | Evans et al. | 361/516 |
| 5,779,699 A | 7/1998 | Lipson | 606/41 |
| 5,779,891 A * | 7/1998 | Andelman | 210/198.2 |
| 5,800,724 A | 9/1998 | Habeger et al. | 216/35 |
| 5,801,917 A * | 9/1998 | Elias | 361/535 |
| 5,814,082 A * | 9/1998 | Fayram et al. | 607/5 |
| 5,867,363 A | 2/1999 | Tsai et al. | 361/502 |
| 5,901,867 A | 5/1999 | Mattson | |
| 5,908,151 A * | 6/1999 | Elias | 228/110.1 |
| 5,922,215 A | 7/1999 | Pless et al. | 216/6 |
| 5,926,357 A * | 7/1999 | Elias et al. | 361/302 |
| 5,926,362 A | 7/1999 | Muffoletto et al. | |
| 5,930,109 A * | 7/1999 | Fishler | 361/508 |
| 5,949,638 A | 9/1999 | Greenwood, Jr. et al. | |
| 5,963,418 A * | 10/1999 | Greenwood et al. | 361/508 |
| 5,968,210 A | 10/1999 | Strange et al. | 29/25.03 |
| 5,973,906 A | 10/1999 | Stevenson et al. | 361/302 |
| 5,983,472 A * | 11/1999 | Fayram et al. | 29/25.42 |
| 6,002,969 A | 12/1999 | Machek et al. | 607/122 |
| 6,006,133 A * | 12/1999 | Lessar et al. | 607/5 |
| 6,009,348 A * | 12/1999 | Rorvick et al. | 607/5 |
| 6,032,075 A * | 2/2000 | Pignato et al. | 607/5 |
| 6,042,624 A * | 3/2000 | Breyen et al. | 29/25.03 |
| 6,052,625 A | 4/2000 | Marshall | 607/122 |
| 6,094,788 A | 8/2000 | Farahmandi et al. | 25/24.41 |
| 6,099,600 A * | 8/2000 | Yan et al. | 29/25.03 |
| 6,104,961 A | 8/2000 | Conger et al. | 607/122 |
| 6,110,233 A * | 8/2000 | O'Phelan et al. | 29/25.03 |
| 6,118,651 A | 9/2000 | Mehrotra et al. | 361/509 |
| 6,141,205 A * | 10/2000 | Nutzman et al. | 361/509 |
| 6,157,531 A * | 12/2000 | Breyen et al. | 361/519 |
| 6,184,160 B1 * | 2/2001 | Yan et al. | 438/800 |
| 6,191,931 B1 * | 2/2001 | Paspa et al. | 361/302 |
| 6,204,476 B1 | 3/2001 | Reynolds et al. | |
| 6,212,063 B1 * | 4/2001 | Johnson et al. | 361/517 |
| 6,249,423 B1 * | 6/2001 | O'Phelan et al. | 361/502 |
| 6,249,709 B1 | 6/2001 | Conger et al. | 607/122 |
| 6,256,542 B1 | 7/2001 | Marshall et al. | 607/126 |
| 6,259,954 B1 | 7/2001 | Conger et al. | 607/122 |
| 6,275,372 B1 | 8/2001 | Vassallo et al. | |
| 6,275,729 B1 * | 8/2001 | O'Phelan et al. | 607/5 |
| 6,297,943 B1 * | 10/2001 | Carson | 361/500 |
| 6,299,752 B1 | 10/2001 | Strange et al. | 205/152 |
| 6,321,114 B1 * | 11/2001 | Nutzman et al. | 607/5 |
| 6,324,049 B1 | 11/2001 | Inagawa et al. | |
| 6,326,587 B1 | 12/2001 | Cardineau et al. | 219/121.68 |
| 6,330,925 B1 | 12/2001 | Ovshinsky et al. | |
| 6,375,688 B1 | 4/2002 | Akami et al. | |
| 6,380,577 B1 | 4/2002 | Cadwallader | |
| 6,388,866 B1 * | 5/2002 | Rorvick et al. | 361/503 |
| 6,402,793 B1 * | 6/2002 | Miltich et al. | 29/25.03 |
| 6,409,776 B1 | 6/2002 | Yan et al. | |
| 6,442,015 B1 | 8/2002 | Niiori et al. | 361/502 |
| 6,451,073 B1 | 9/2002 | Farahmandi et al. | |
| 6,459,566 B1 | 10/2002 | Casby et al. | |
| 6,477,037 B1 * | 11/2002 | Nielsen et al. | 361/520 |
| 6,493,212 B1 * | 12/2002 | Clarke et al. | 361/521 |
| 6,509,588 B1 * | 1/2003 | O'Phelan et al. | 257/209 |
| 6,522,525 B1 | 2/2003 | O'Phelan et al. | 361/509 |
| 6,556,863 B1 | 4/2003 | O'Phelan et al. | |
| 6,571,126 B1 | 5/2003 | O'Phelan et al. | 607/5 |
| 6,585,152 B2 | 7/2003 | Farahmandi et al. | |
| 6,628,505 B1 | 9/2003 | Andelman | |
| 6,631,072 B1 | 10/2003 | Paul et al. | |
| 6,674,634 B2 | 1/2004 | O'Phelan et al. | 361/509 |
| 6,684,102 B1 | 1/2004 | O'Phelan et al. | 607/5 |
| 6,687,118 B1 | 2/2004 | O'Phelan et al. | 361/508 |
| 6,699,265 B1 * | 3/2004 | O'Phelan et al. | 607/1 |
| 6,709,946 B2 * | 3/2004 | O'Phelan et al. | 438/396 |
| 6,763,265 B2 | 7/2004 | O'Phelan et al. | |
| 6,795,729 B1 | 9/2004 | Breyen et al. | |
| 6,833,987 B1 | 12/2004 | O'Phelan | |
| 6,885,548 B2 * | 4/2005 | Nyberg | 361/523 |
| 6,885,887 B2 * | 4/2005 | O'Phelan et al. | 607/5 |
| 6,957,103 B2 * | 10/2005 | Schmidt et al. | 607/5 |
| 6,985,351 B2 * | 1/2006 | O'Phelan et al. | 361/509 |
| 6,990,375 B2 * | 1/2006 | Kloss et al. | 607/20 |
| 6,999,304 B2 * | 2/2006 | Schmidt et al. | 361/528 |
| 7,072,713 B2 * | 7/2006 | O'Phelan et al. | 607/10 |
| 7,079,897 B2 * | 7/2006 | Sun et al. | 607/19 |
| 7,107,099 B1 * | 9/2006 | O'Phelan et al. | 607/5 |
| 7,120,008 B2 * | 10/2006 | Sherwood | 361/301.4 |
| 7,154,739 B2 * | 12/2006 | O'Phelan | 361/508 |
| 7,157,671 B2 * | 1/2007 | O'Phelan et al. | 219/535 |
| 7,177,692 B2 * | 2/2007 | O'Phelan et al. | 607/36 |
| 7,180,727 B2 * | 2/2007 | Poplett | 361/508 |
| 7,190,569 B2 * | 3/2007 | O'Phelan et al. | 361/509 |
| 7,190,570 B2 * | 3/2007 | Schmidt et al. | 361/520 |
| 7,221,556 B2 | 5/2007 | Schmidt et al. | |
| 2003/0030969 A1 | 2/2003 | Farahmandi et al. | |
| 2003/0072124 A1 * | 4/2003 | O'Phelan et al. | 361/301.4 |
| 2003/0165744 A1 | 9/2003 | Schubert et al. | |

| | | | |
|---|---|---|---|
| 2003/0195568 A1 | 10/2003 | O'Phelan et al. ............... 607/5 | |
| 2004/0019268 A1 | 1/2004 | Schmidt et al. | |
| 2004/0032698 A1 | 2/2004 | Paul et al. | |
| 2004/0114311 A1 | 6/2004 | O'Phelan et al. | |
| 2004/0147960 A1* | 7/2004 | O'Phelan et al. ............... 607/1 | |
| 2004/0147961 A1* | 7/2004 | O'Phelan et al. ............... 607/1 | |
| 2004/0173835 A1* | 9/2004 | Schmidt et al. ............. 257/301 | |
| 2004/0174658 A1 | 9/2004 | O'Phelan et al. | |
| 2004/0193221 A1 | 9/2004 | O'Phelan et al. | |
| 2004/0215281 A1 | 10/2004 | O'Phelan et al. | |
| 2004/0220627 A1 | 11/2004 | Crespi et al. | |
| 2005/0010253 A1 | 1/2005 | O'Phelan et al. | |
| 2005/0017888 A1* | 1/2005 | Sherwood et al. ........... 341/155 | |
| 2005/0052825 A1 | 3/2005 | O'Phelan | |
| 2005/0221171 A1 | 10/2005 | Haasl et al. | |
| 2006/0009808 A1 | 1/2006 | Schmidt et al. | |
| 2006/0012942 A1 | 1/2006 | Poplett | |
| 2006/0107506 A1 | 5/2006 | Doffing et al. | |
| 2006/0152887 A1* | 7/2006 | Schmidt et al. ............. 361/528 | |
| 2006/0174463 A1 | 8/2006 | O'Phelan et al. | |
| 2006/0247715 A1 | 11/2006 | Youker | |
| 2007/0118182 A1 | 5/2007 | O'Phelan | |

FOREIGN PATENT DOCUMENTS

| | | |
|---|---|---|
| GB | 825900 | 12/1959 |
| GB | 2132019 | 6/1984 |
| JP | 52-004051 | 1/1977 |
| JP | 05-074664 | 3/1993 |
| WO | WO-9854739 A1 | 12/1998 |
| WO | WO-99/51302 | 10/1999 |
| WO | WO-9951302 A1 | 10/1999 |
| WO | WO-00/19470 | 4/2000 |
| WO | WO-0019470 A1 | 4/2000 |
| WO | WO-0237515 A2 | 5/2002 |
| WO | WO-2006002148 A1 | 1/2006 |

OTHER PUBLICATIONS

Block, Michael, "Biphasic Defibrillation Using a Single Capacitor with Large Capacitance: Reduction of Peak Voltages and ICD Device Size", *PACE*, Vo. 19, (Feb. 1996),207-214.

Block, Michael, "Internal Defibrillation with Smaller Capacitors: A Prospective Randomized Cross-Over Comparison of Defibrillation Efficacy Obtained with 90-iF and 125-iF Capacitors in Humans", *Journal of Cardiovascular Electrophysiology*, vol. 6, No. 5, (May 1995),333-342.

Brugada, J., "Clinical evaluation of defibrillation efficacy with a new single-capacitor biphasic waveform in patients undergoing implantation of an implantable cardioverter defibrillator", *The European Society of Cardiology*, vol. 3, (Oct. 2001),278-284.

Doffing, B., et al., "Method and Apparatus for Providing Flexible Partially Etched Capacitor Electrode Interconnect", U.S. Appl. No. 10/996,903, filed Nov. 24, 2004, 239 Pgs.

Haasl, Benjamin J., et al., "Insulative Member on Battery Cathode", U.S. Appl. No. 11/140,854, filed May 31, 2005, 30 Pages.

Hahn, Stephen J., et al., "Large Capacitor Defibrillation Waveform Reduces Peak Voltages Without Increasing Energies", *PACE*, vol. 18, Part II, (Jan. 1995),203-207.

Kelley, Shawn, et al., "Method and Apparatus for Porous Insulative Film for Insulating Energy Source Layers", U.S. Appl. No. 11/127,025, filed May 11, 2005, 21 Pages.

Morley, A. R., et al., "Electrolytic capacitors: their fabrication and the interpretation of their operations behaviour", *The Radio and Electronic Engineer*, vol. 43, No. 7,(Jul. 1973),421-429.

O'Phelan, Michael J., "Flat Capacitor Having an Active Case", U.S. Appl. No. 10/969,441, filed Oct. 20, 2004, 44 pgs.

Poplett, J. M., "Capacitor With Single Sided Partial Etch and Stake", U.S. Appl. No. 11/065,873, filed Feb. 25, 2005, 28 pgs.

Youker, Nick A., "Method and Apparatus for an Implantable Pulse Generator With a Stacked Battery and Capacitor", U.S. Appl. No. 11/117,952, filed Apr. 29, 2005, 21 Pages.

O'Phelan, Michael J., et al., "Batteries Including a Flat Plate Design", U.S. Appl. No. 10/360,551, filed Feb. 7, 2003, 121 pgs.

O'Phelan, Michael, et al., "Capacitor Having a Feedthrough Assembly With a Coupling Member", U.S. Appl. No. 10/846,805, filed May 14, 2004, 39 pgs.

O'Phelan, Michael J., et al., "Capacitor Having a Feedthrough Assembly With a Coupling Member", U.S. Appl. No. 09/706,579, filed Nov. 3, 2000, 29 pgs.

O'Phelan, Michael J., et al., "Flat Capacitor for an Implantable Medical Device", U.S. Appl. No. 10/758,701, filed Jan. 15, 2004, 219 pgs.

O'Phelan, Michael J., et al., "Flat Capacitor for an Implantable Medical Device", U.S. Appl. No. 10/758,677, filed Jan. 15, 2004, 219 pgs.

O'Phelan, Michael J., "Flat Capacitor Having an Active Case", U.S. Appl. No. 09/706,517, filed Nov. 3, 2000, 39 pgs.

O'Phelan, Michael J., et al., "Flat Capacitor Having Staked Foils and Edge-Connected Connection Members", U.S. Appl. No. 10/728,655, filed Dec. 5, 2003, 65 pgs.

O'Phelan, Michael J., et al., "Implantable Heart Monitors Having Capacitors With Endcap Headers", U.S. Appl. No. 10/736,209, filed Dec. 15, 2003, 19 pgs.

O'Phelan, Michael J., et al., "Implantable Heart Monitors Having Flat Capacitors With Curved Profiles", U.S. Appl. No. 10/729,424, filed Dec. 4, 2003, 28 pgs.

Schmidt, Brian L., et al., "Configurations and Methods for Making Capacitor Connections", filed Nov. 3, 2000, 25 pgs.

Schmidt, Brian, et al., "Method for Interconnecting Anodes and Cathodes in a Flat Capacitor", U.S. Appl. No. 11/325,931, filed Jan. 5, 2006, 28 Pages.

"U.S. Appl. No. 09/706,519 (Atty. Ref. 279.339US1) Non Final Office Action mailed Apr. 24, 2002", 8 pgs.

"U.S. Appl. No. 09/706,519 (Atty. Ref. 279.339US1) Notice of Allowance mailed Aug. 26, 2002", 9 pgs.

"U.S. Appl. No. 09/706,519 (Atty. Ref. 279.339US1) Response filed Jul. 24, 2002 to Non Final Office Action mailed Apr. 24, 2002", 4 pgs.

"U.S. Appl. No. 10/299,234 (Atty. Ref. 279.339US2) Notice of Allowance mailed Sep. 25, 2003", 9 pgs.

"U.S. Appl. No. 10/299,234 (Atty. Ref. 279.339US2) Preliminary Amendment filed Nov. 19, 2002", 2 pgs.

"U.S. Appl. No. 10/804,288 (Atty. Ref. 279.339US3) Notice of Allowance mailed Aug. 23, 2005", 24 pgs.

"U.S. Appl. No. 10/804,288 (Atty. Ref. 279.339US3) Preliminary Amendment filed Mar. 18, 2004", 5 pgs.

"U.S. Appl. No. 11/325,931 (Atty. Ref. 279.339US4) Non Final Office Action mailed Jul. 21, 2006", 7 pgs.

"U.S. Appl. No. 11/325,931 (Atty. Ref. 279.339US4) Notice of Allowance mailed Jan. 16, 2007", 15 pgs.

"U.S. Appl. No. 11/325,931 (Atty. Ref. 279.339US4) Response filed Oct. 23, 2006 to Non Final Office Action mailed Jul. 21, 2006", 9 pgs.

"PCT Application No. PCT/US01/45202 (Atty Ref 279.339WO1), International Search mailed Feb. 21, 2003", 6 pgs.

"PCT Application No. PCT/US2005.021898 (Atty Ref 279.823WO1), International Preliminary Report on Patentability mailed Jan. 11, 2007", 7 pgs.

"PCT Application No. PCT/US2005.021898 (Atty Ref 279.823WO1), International Search Report mailed Mar. 11, 2005", 4 pgs.

* cited by examiner

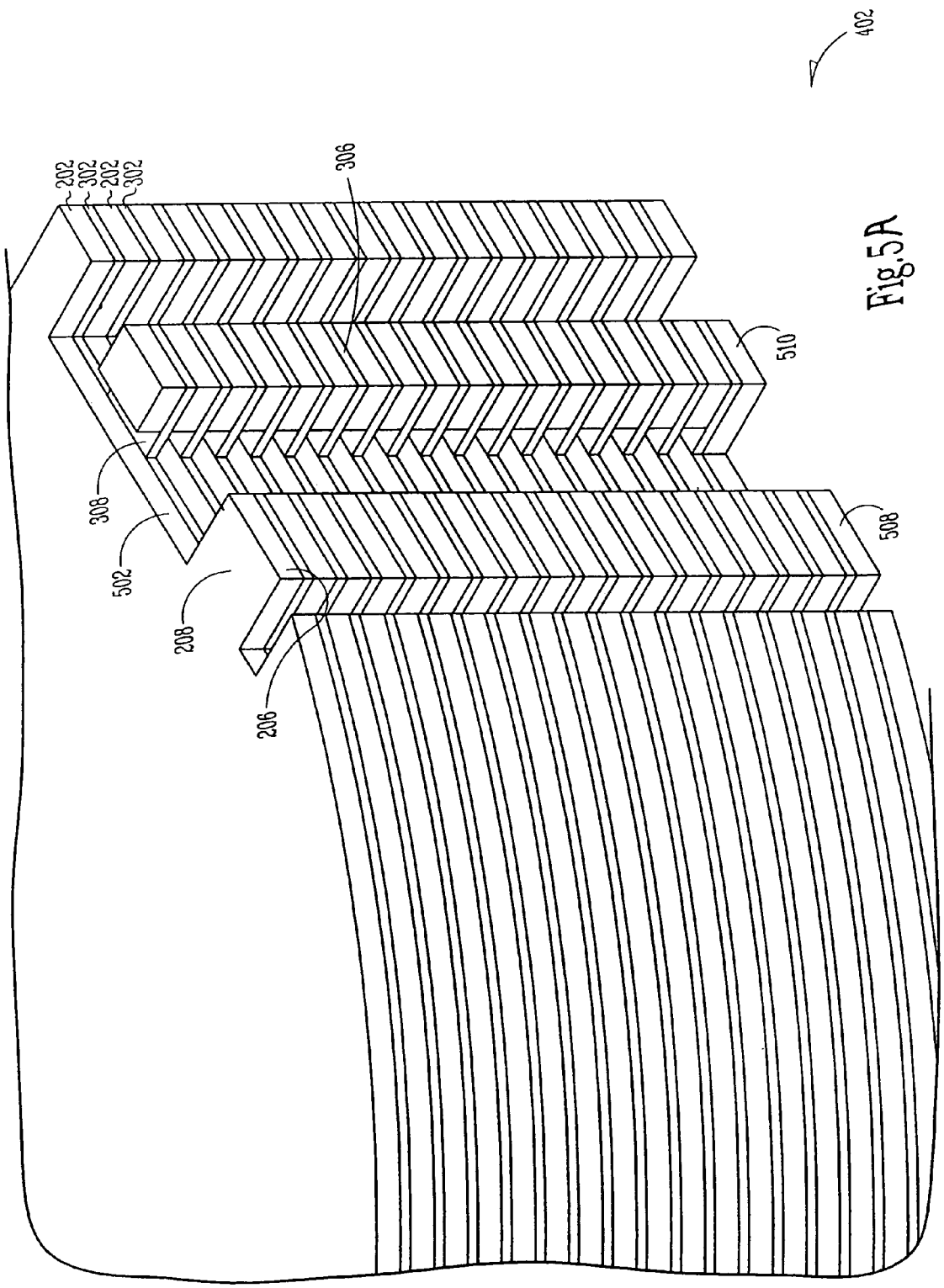

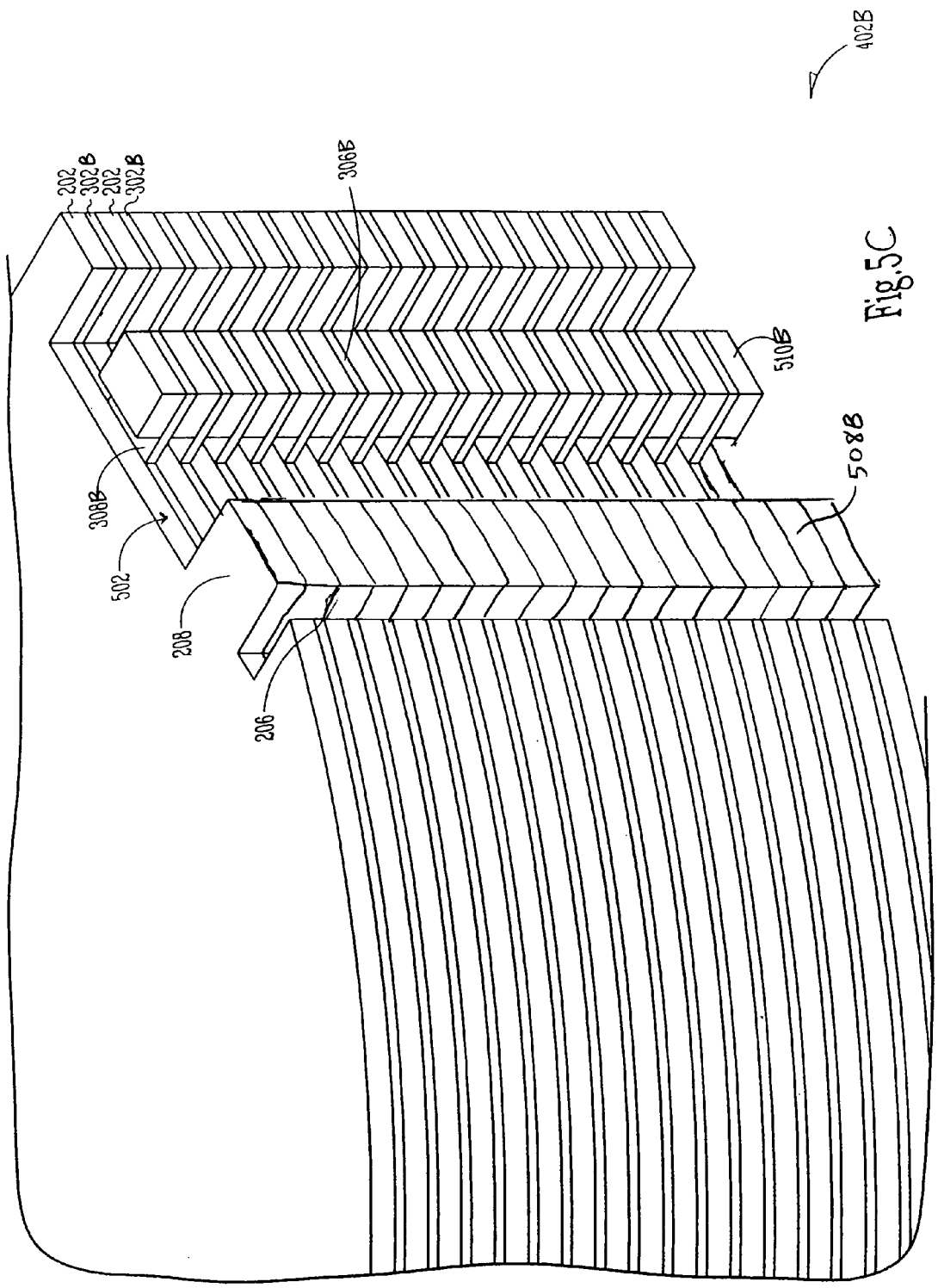

METHOD FOR INTERCONNECTING ANODES AND CATHODES IN A FLAT CAPACITOR

CROSS-REFERENCE TO RELATED APPLICATIONS

This application is a continuation-in-part of U.S. application Ser. No. 10/804,288, filed on Mar. 18, 2004, now issued as U.S. Pat. No. 6,999,304, which is a divisional of U.S. application Ser. No. 10/299,234, filed Nov. 19, 2002, now issued as U.S. Pat. No. 6,709,946, which is a divisional of U.S. application Ser. No. 09/706,519, filed Nov. 3, 2000, now issued as U.S. Pat. No. 6,509,588, the specifications of which are hereby incorporated by reference.

FIELD OF THE INVENTION

The present invention concerns implantable medical devices, such as defibrillators and cardioverters, particularly structures and methods for capacitors in such devices.

BACKGROUND

Capacitors have undergone substantial improvement over the years. Smaller capacitors are in demand for various applications. One such application is for biomedical implants. For example, defibrillators and pacemakers use capacitors for pulse delivery.

The defibrillator or cardioverter includes a set of electrical leads, which extend from a sealed housing into the walls of a heart after implantation. Within the housing are a battery for supplying power, monitoring circuitry for detecting abnormal heart rhythms, and a capacitor for delivering bursts of electric current through the leads to the heart.

The capacitor can take the form of a flat aluminum electrolytic capacitor. Flat capacitors include a stack of flat capacitor elements mounted within a capacitor case. Each flat capacitor element includes one or more separators between two sheets of aluminum foil. One of the aluminum foils serves as a cathode (negative) foil, and the other serves as an anode (positive) foil. The capacitor elements each have an individual capacitance (or energy-storage capacity) proportional to the surface area of the foil.

One drawback in manufacturing such capacitors is that each of the anodes and each of the cathodes must be connected together. For instance, all the anodes are crimped or welded together and attached to a feedthrough terminal for connection to circuitry outside the capacitor case. Another process is also done for the cathode foils in the capacitor stack. Errors during the manufacturing steps may cause defects in the capacitor or decrease the reliability of the capacitor after it is constructed. Another drawback is that the interconnections take up space within the capacitor. This increases the size of the capacitor, which is undesirable when the capacitors are used for implantable medical devices such as defibrillators.

Thus, what is needed is a simple way to provide the anode and cathode interconnections of capacitors with as few steps as possible and which lends itself to mass producing said capacitors.

SUMMARY

In one embodiment, a method includes stacking a plurality of cathodes layers and a plurality of anode layers such that a cathode connection member on each of the cathode layers at least partially overlays an anode connection member on each of the anode layers, connecting the cathode connection members together with the anode connection members, and electrically isolating the anode layers from the cathode layers.

In one aspect, a capacitor stack includes a plurality of cathode layers having cathode connection members and a plurality of anode layers having anode connection members. The anode connection members are connected to the cathode connection members and configured such that the anode layers can be electrically separated from the cathode layers by cutting only the anode connection members or the cathode connection members.

This Summary is an overview of some of the teachings of the present application and not intended to be an exclusive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scop of the present invention is defined by the appended claims and their equivalents.

BRIEF DESCRIPTION OF THE DRAWINGS

FIG. 5A is a perspective view of the stack of FIG. 4 after the stack has been processed according to one embodiment of the present invention.

FIG. 5C is a perspective view of the stack of FIG. 5B after the stack has been processed according to one embodiment of the present invention.

DETAILED DESCRIPTION

The following detailed description, which references and incorporates the figures, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

Figure 1:
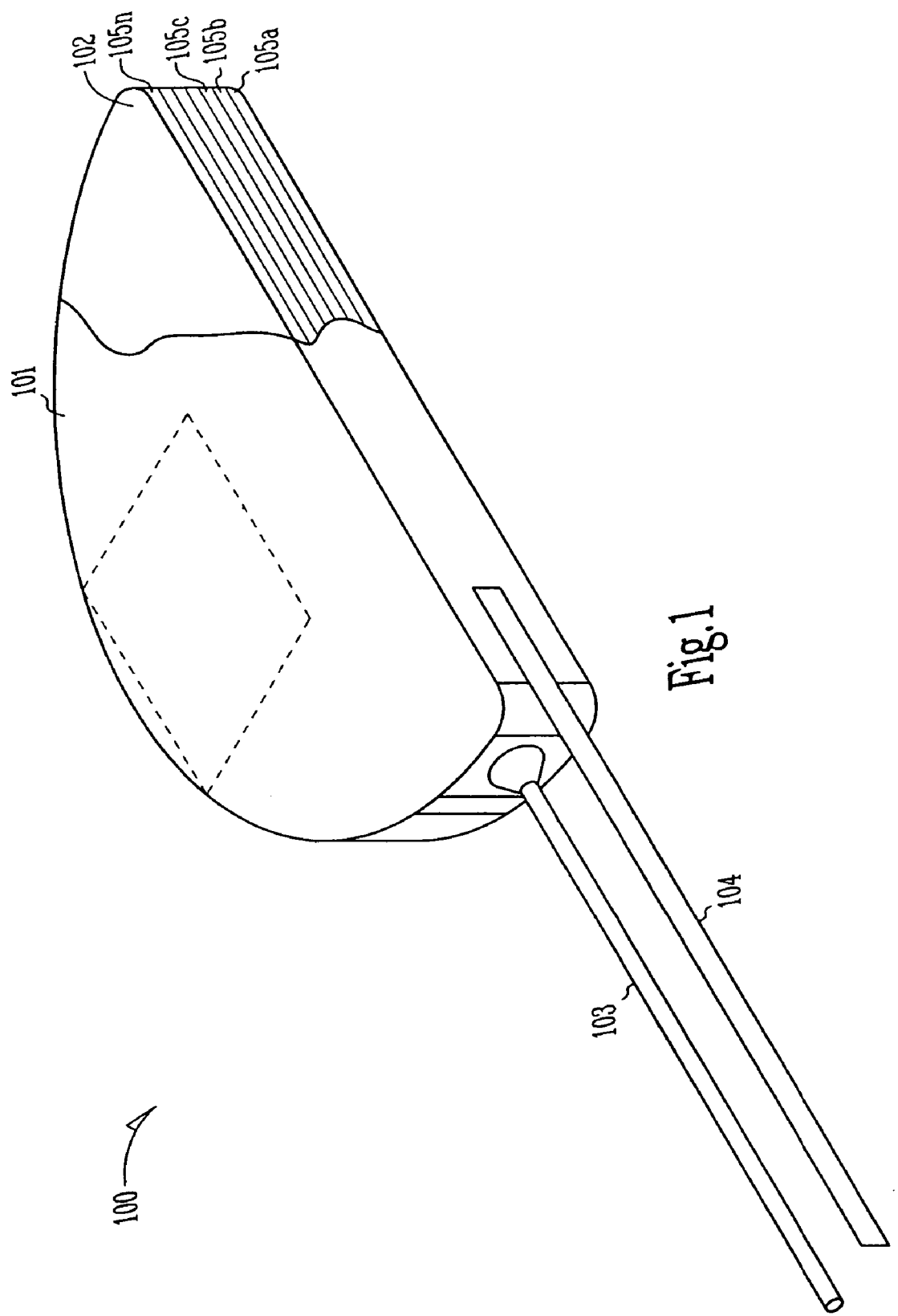
FIG. 1 is an isometric view of a flat capacitor according to one embodiment of the present invention.

FIG. 1 shows a flat capacitor 100 constructed according to one embodiment of the present invention. Although capacitor 100 is a D-shaped capacitor, in other embodiments, the capacitor is another desirable shape, including, but not limited to rectangular, circular, oval or other symmetrical or asymmetrical shape. Capacitor 100 includes a case 101 which contains a capacitor stack 102. In the exemplary embodiment, case 101 is manufactured from a conductive material, such as aluminum. In other embodiments, the case is manufactured using a nonconductive material, such as a ceramic or a plastic.

Capacitor 100 includes a first terminal 103 and a second terminal 104 for connecting capacitor stack 102 to an outside electrical component, such as heart monitor circuitry, including defibrillator, cardioverter, and pacemaker circuitry. In the exemplary embodiment, terminal 103 is a feedthrough terminal insulated from case 101, while terminal 104 is directly connected to case 101. In other embodiments, the capacitor incorporates other connection methods, depending on other design factors. For instance, in some embodiments, capacitor 100 includes two or more feedthrough terminals 103.

Capacitor stack 102 includes capacitor elements 105a, 105b, 105c, . . . , 105n, with each capacitor element 105a-105n including one or more cathodes, anodes, and separators. Each cathode is a foil structure and can include aluminum, tantalum, hafnium, niobium, titanium, zirconium, and combinations of these metals. In one embodiment, each cathode of capacitor stack 102 is connected to the other cathodes by welding or other connection methods which will be discussed below. The cathodes are coupled to conductive case 101, and terminal 104 is attached to case 101 to provide a cathode connection to outside circuitry. In some embodiments, the cathode is coupled to a feedthrough conductor extending through a feedthrough hole.

The separator is located between each anode and cathode. In one embodiment, the separator includes one or more sheets of kraft paper impregnated with an electrolyte. In one embodiment, the separator includes two sheets of paper. The electrolyte can be any suitable electrolyte for an electrolytic capacitor, such as an ethylene-glycol base combined with polyphosphates, ammonium pentaborate, and/or an adipic acid solute.

In one embodiment, one or more of the anodes of capacitor stack 102 is a multi-anode stack which includes three foil layers. In other embodiments, one or more anode stacks include one, two, three or more anode foils having a variety of anode shapes. The anode foils are generally foil structures and can include aluminum, tantalum, hafnium, niobium, titanium, zirconium, and combinations of these metals. In one embodiment, at least portions of a major surface of each anode foil is roughened or etched to increase its effective surface area. This increases the capacitive effect of the foil with no relative increase in volume. Other embodiments incorporate other foil compositions and/or classes of foil compositions.

In one embodiment, each anode is connected to the other anodes of the capacitor and coupled to feedthrough assembly 103 for electrically connecting the anode to circuitry outside the case. In some embodiments, the anodes are connected to the case and the cathodes are coupled to a feedthrough assembly. In other embodiments, both the anode and the cathode are connected to feedthroughs.

Figure 2A:
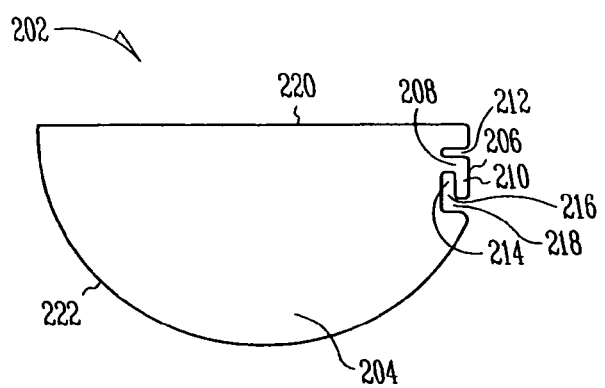
FIG. 2A is a top view of an anode foil for use in constructing a capacitor according to one embodiment of the present invention.

FIG. 2A shows an anode 202 according to one embodiment of the present invention. Anode 202 is shown before it is assembled into capacitor stack 102 as shown in FIG. 1. Anode 202 includes a main body portion 204 having one or more connection members 206. In one embodiment, connection member 206 includes one or more separate members attached to the anode by welding, staking, or other connection method.

In other embodiments, connection member 206 is an integral portion of anode 202, and is punched, laser-cut, or otherwise shaped from the anode foil. In such an embodiment, portions of connection member 206 are not etched along with the rest of anode 202. For instance, a chemical mask is put on portions of connection member 206 to keep those masked portions from becoming etched during the etching process. As will be discussed below, this provides that those unetched, non-porous sections make welding the edges of the anodes to each other easier.

Connection member 206 includes a proximal section 208 and distal section 210. In the embodiment of FIG. 2A, connection member 206 is an L-shaped member. However, it can also be hook shaped, U-shaped, and/or have other shape. In one embodiment, a portion of a distal section 210 along its outer edge is unetched, as discussed above.

In one embodiment, proximal section 208 is connected to main body 204 and is defined in part by a pair of cut-out portions 212 and 214 located on opposing sides of proximal section 208. Distal section 210 is connected to a portion of proximal section 208. In one embodiment, it is integral with proximal section 208. In some embodiments, distal section 210 is attached as a separate member. In one embodiment, distal section 210 is defined in part by a cut-out portion 216 which is located between main body 204 and distal section 210, and a cut-out portion 218 which separates distal section 210 from main body 204.

In this embodiment, connection member 206 is located within the general perimeter or outline of anode 202. In other embodiments, connection member extends further from the main body of anode 202 or connection member 206 is more internal within the main body of anode 202.

In some embodiments, each anode foil in capacitor stack 102 includes an connection member such as connection member 206. In other embodiments, one or more anode foils in a multi-anode stack have a connection member 206 while the other anode foils in the multi-anode stack are connected to the anode having the connection member. For instance, in one embodiment, a three-foil anode stack includes one foil having a connection member 206 and two foils without connection members. The two foils without connection members are welded, staked, or otherwise attached to the foil having the connection member.

Figure 2B:
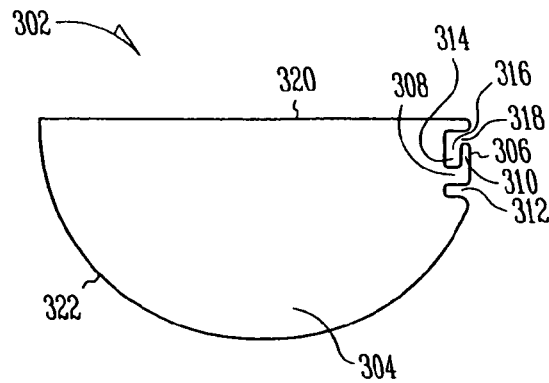
FIG. 2B is a top view of a cathode foil for use in constructing a capacitor according to one embodiment of the present invention.

FIG. 2B shows a cathode 302 according to one embodiment of the present invention. Cathode 302 is shown before it is assembled into capacitor stack 102 as shown in FIG. 1. Cathode 302 includes a main body portion 304 having one or more connection members 306. In one embodiment, connection member 306 is an integral portion of cathode 302, and is punched, laser-cut, or otherwise shaped from the anode foil. In one embodiment, connection member 306 includes one or more separate members attached to the anode by welding, staking, or other connection method.

In one embodiment, connection member 306 includes a proximal section 308 and a distal section 310. In the embodiment of FIG. 2B, connection member 306 is an L-shaped member. However, in some embodiments it is hook shaped, U-shaped, and/or have other shape.

In one embodiment, proximal section 308 is connected to main body 304 and is defined in part by a pair of cut-out portions 312 and 314 located on opposing sides of proximal section 308. Distal section 310 is connected to a portion of proximal section 308. In one embodiment, it is integral with proximal section 308. In some embodiments, distal section 310 is attached as a separate member. In one embodiment, distal section 310 is defined in part by a cut-out portion 316 which is located between main body 304 and distal section 310, and a cut-out portion 318 which separates distal section 310 from main body 304.

In this embodiment, connection member 306 is located within the general perimeter or outline of cathode 302. In other embodiments, connection member 306 extends further from the main body of cathode 302 or connection member 306 is more internal within the main body of cathode 302.

Figure 3A:
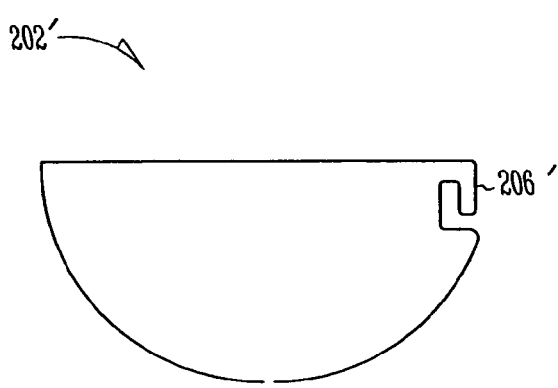
FIG. 3A is a top view of an anode foil for use in constructing a capacitor according to one embodiment of the present invention.
Figure 3B:
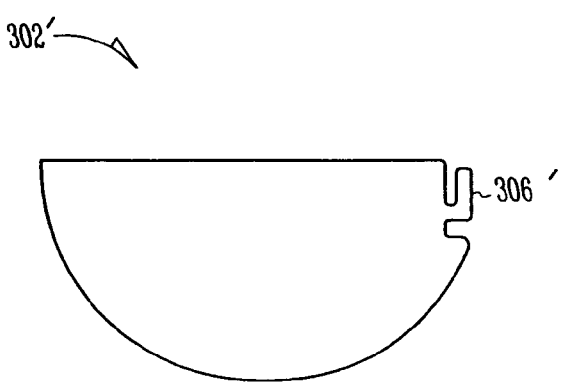
FIG. 3B is a top view of a cathode foil for use in constructing a capacitor according to one embodiment of the present invention.

FIGS. 3A and 3B show an anode 202' and a cathode 302' according to one embodiment of the present invention. Anode 202' and cathode 302' are shown before being assembled into capacitor stack 102 as shown in FIG. 1. Anode 202' and cathode 302' are generally similar to anode 202 and cathode 302, respectively, except connection member 206' does not include a cut-out such as cut-out 212 of anode 202 and connection member 306' does not include a cut-out such as cut-out 318 of cathode 302. Other embodiments utilize other shapes and locations for connection members such as connection members 206, 206', 306, and 306'.

For instance, in various embodiments, connection members 206 and 306 may be in different positions along the edges or even within the main body portions of the capacitor foils 202 and 302. For instance, in some embodiments connection members 206 and 306 are located along edges 220 and 320 of the respective foils 202 and 302. In some embodiments, the portions are located along curved edges 222 and 322 of the respective foils 202 and 302. In other embodiments, the portions may be cut-out within main bodies 204 and 304.

In one embodiment, proximal section 308 of cathode 302 and proximal section 208 of anode 202 are located in different positions (relative to each other) on their respective foils, while distal sections 210 and 310 are generally commonly positioned. For instance, in one embodiment connection members 206 and 306 of the anode 202 and the cathode 302, respectively, are mirror images of each other. In some embodiments, connection members 206 and 306 have generally reverse images of each other. In some embodiments, connection members 206 and 306 can have different shapes or sizes relative to each other. For example, the distal portions on either the anode or the cathode can longer or shorter than its opposing distal portion.

Figure 4:
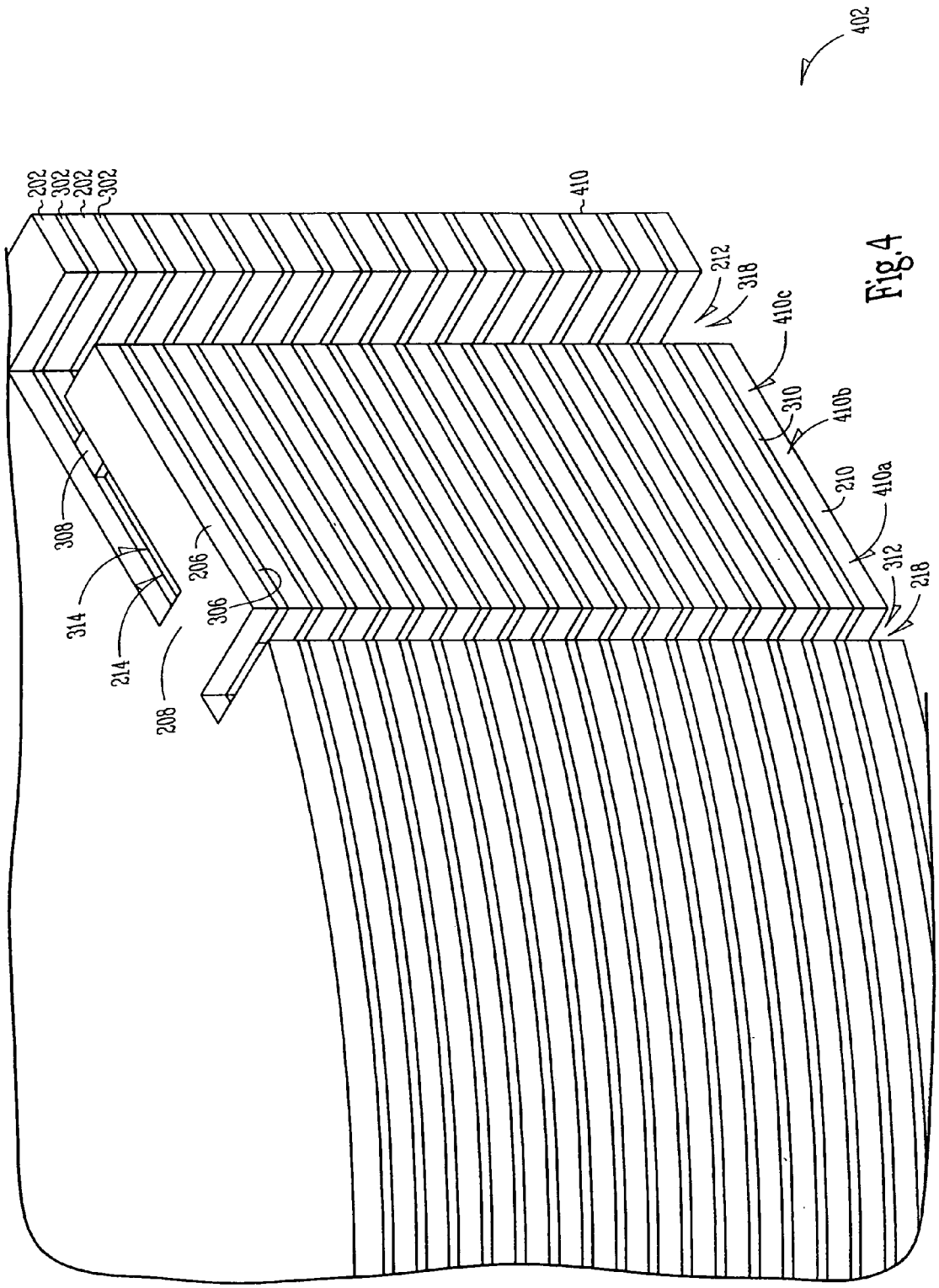
FIG. 4 is a perspective view of a stack of one or more anodes and cathodes of FIGS. 2A and 2B.

FIG. 4 shows a stack 402 of one or more alternating anodes 202 and cathodes 302. As shown in FIG. 4, connection members 206 and 306 are overlaying and underlying each other. As used herein, overlay and underlay refer to the position or location of portions of the foils which are commonly positioned from a top view. In the embodiment of FIG. 4, it is seen that connection members 206 and 306 have some commonly positioned portions relative to each other and some portions which are exclusively positioned relative to each other.

For instance, proximal sections 208 of anodes 202 are exclusively positioned or located. This means that at least a portion of proximal sections 208 do not overlay or underlay a portion of cathodes 203. Likewise, proximal sections 308 of cathodes 302 are exclusive portions and include at least a portion not overlaying or underlaying a portion of anode 202. Conversely, distal sections 210 and 310 are commonly positioned and each include at least a portion overlaying or underlaying each another. Cut-out portions 214 and 314 are also commonly positioned. Cut-out 218 is commonly positioned with cut-out 312 while cut-out 212 is commonly positioned with cut-out 318.

When stacked as shown in FIG. 4, the edges of distal sections 210 and 310 form a surface 410. In this embodiment, surface 410 can generally be described as having a first portion 410a which fronts the proximal sections 208 of anodes 202, a second portion 410b which fronts common cut-portions 214 and 314, and third portion 410c which fronts the proximal sections 308 of cathodes 302.

In this embodiment, distal sections 210 and 310 of anode connection member 206 and cathode connection member 306 are fully overlaying one another. Fully overlaying means that there are generally no gaps along surface 410 of stack 402 when the anodes and cathodes are stacked as in FIG. 4. The fully overlaid structure of stack 402 provides a complete surface 410 which provides for ease of edge-welding or otherwise connecting connection members 206 and 306 together, as will be described below. As will be discussed below, other embodiments leave one or more gaps in surface 410 when the anodes and cathodes are stacked. For instance, in some embodiments, one or more of distal sections 210 or 310 may not reach all the way across front surface 410.

After being stacked as discussed above, at least portions of connection members 206 and 306 are connected to each other. For instance, in one embodiment portions of distal sections 210 and 310 are connected to each other. In one embodiment, distal sections 210 and 310 are edge-welded all along surface 410. In one embodiment, distal sections 210 and 310 are only connected along portion 410a and 410c of surface 410. In one embodiment, distal sections 210 and 310 are soldered along surface 410. In some embodiments, portions of distal sections 310 and 210 are staked, swaged, laser-welded, or connected by an electrically conductive adhesive. In other embodiments, portions of proximal sections 208 are connected to each other and/or portions of proximal sections 308 are connected to each other.

After being connected, portions of connection members 206 and 306 are removed or separated so that proximal sections 208 and 308 are electrically isolated from each other. As used herein, electrically isolated means that sections 208 and 308 are electrically insulated from each other at least up to a surge voltage of capacitor 100.

FIG. 5A shows stack 402 after portions of distal sections 210 and 310 have been removed from the stack, forming a separation 502 between anode connection members 206, which together comprise anode connection section 508, and cathode connection members 306, which together comprise cathode connection section 510. Separation 502 in the present embodiment electrically isolates section 508 from section 510. Proximal sections 308 are still electrically coupled to each other as are proximal sections 208. In some embodiments, separation 502 is a thin slice. In some embodiments, separation 502 is as wide as cut-outs 214 and 314, as shown in FIG. 4. In some embodiments, an electrically insulative material is inserted in separation 502. In various embodiments, separation 502 is formed by laser cutting, punching, and/or tool or machine cutting.

Figure 5B:
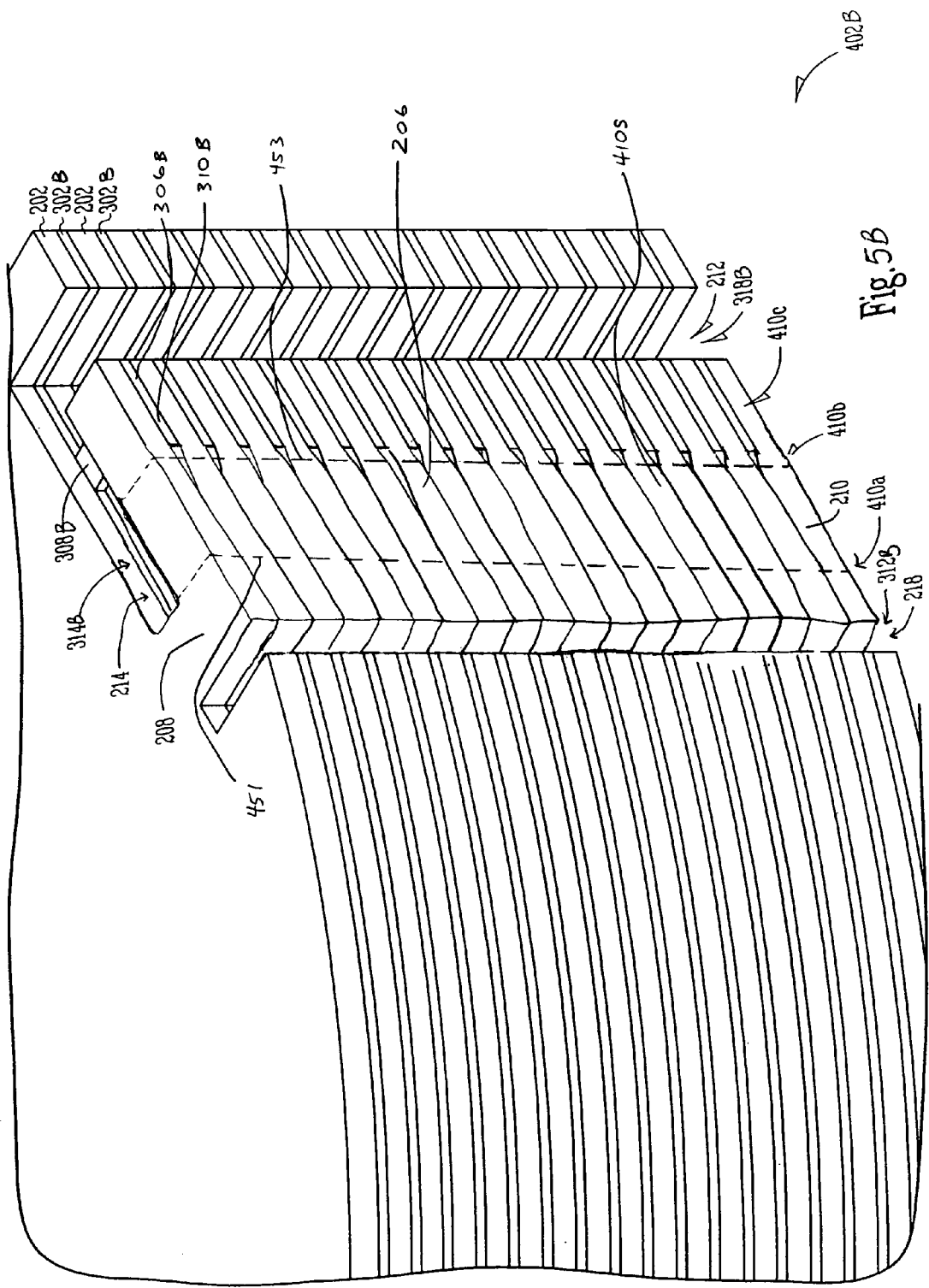
FIG. 5B is a perspective view of a stack of anodes and cathodes according to one embodiment.

FIG. 5B shows a stack 402B of one or more alternating anodes 202 and cathodes 302B, in accordance with one embodiment. Anodes 202 are as discussed above. In this example, cathodes 302B can include the features discussed above for other cathodes and the above discussion is incorporated herein. Cathodes 302B have a shorter distal section 310B than the example discussed above in FIG. 4, for example. Distal section 310B can be L-shaped as discussed above or the connection member can be straight out from the cathode body forming an I-shape. As shown in FIG. 5B, connection members 206 and 306B include at least a portion that is overlaying and underlying each other. As noted above, overlay and underlay refer to the position or location of portions of the foils which are commonly positioned from a top view. In the embodiment of FIG. 5B, it is seen that connection members 206 and 306B have some commonly positioned portions relative to each other and some portions which are exclusively positioned relative to each other.

For instance, proximal sections 208 of anodes 202 are exclusively positioned or located. This means that at least a portion of proximal sections 208 do not overlay or underlay a portion of cathodes 302B. Likewise, in one embodiment, proximal sections 308B of cathodes 302B are exclusive portions and include at least a portion not overlaying or underlaying a portion of anode 202. Moreover, in this example, distal portion 310B of cathodes 302B does not extend across the entire distal portion 210 of the anodes 202. Distal sections 210 and 310B do include a commonly positioned portion along portion 410c where each include at least a portion overlaying or underlaying each another. Cut-out portions 214 and 314B are also commonly positioned. Cut-out 218 is commonly positioned with cut-out 312B while cut-out 212 is commonly positioned with cut-out 318B.

When stacked as shown in FIG. 5B, the edges of distal sections 210 and 310B form a surface 410S. In this embodiment, surface 410S can generally be described as having a first portion 410a which fronts the proximal sections 208 of anodes 202, a second portion 410b which fronts common cut-portions 214 and 314B, and third portion 410c which fronts the proximal sections 308B of cathodes 302B.

In this embodiment, distal sections 210 and 310B of anode connection member 206 and cathode connection member 306B are overlaid relative to each other such as to be not continuous across surface 410S, with anode connection members 206 reaching across surface 410S but cathode connection members 306B not reaching across the surface. In other embodiments, the reverse can be true and the cathode connection member can reach across while the anode connection member is shorter and does not reach across.

After being stacked as discussed above, at least portions of connection members 206 and 306B are connected to each other. For instance, in one embodiment portions of distal sections 210 and 310B are connected to each other. In one embodiment, distal sections 210 and 310B are edge-welded all along surface 410S. In one embodiment, distal sections 210 and 310B are only connected along portion 410a and 41c of surface 410S. In one embodiment, distal sections 210 and 310B are soldered along surface 410S. In some embodiments, portions of distal sections 310B and 210 are staked, swaged, laser-welded, or connected by an electrically conductive adhesive. In other embodiments, portions of proximal sections 208 are connected to each other and/or portions of proximal sections 308B are connected to each other.

After being connected, portions of connection members 206 and 306B are removed or separated so that proximal sections 208 and 308B are electrically isolated from each other. As used herein, electrically isolated means that sections 208 and 308B are electrically insulated from each other at least up to a surge voltage of capacitor 100 (FIG. 1). For example, dashed lines 451 and 453 define an example of an area that can be removed to electrically isolate the anodes and the cathodes. In various embodiments, different areas can be removed. For example, in one embodiment, a portion of the distal ends 210 of the anodes are removed and the cathode distal sections are not removed at all. In another embodiment, a portion of the commonly positioned section 410c can be removed. Some examples include removing a portion of the distal section 210 of the anode connection member 206 and a portion of the distal section 310B of the cathode connection member 306B. Some examples include removing a portion of the distal section 210 of the anode connection member 206 such that there remains no material or section of the cathode connection member 306B adjacent the anode connection member 206.

FIG. 5C shows stack 402B after portions of distal sections 210 have been removed from the stack, forming a separation 502 between anode connection members 206, which together comprise anode connection section 508B, and cathode connection members 306B, which together comprise cathode connection section 510B. Separation 502 in the present embodiment electrically isolates section 508B from section 510B. Proximal sections 308B are still electrically coupled to each other as are proximal sections 208. In one embodiment, the separation is performed such that cathode connection members 306B include some anode material between each layer, while anode connection members 206 do not include any cathode material between the layers.

In some embodiments, separation 502 is a thin slice. In some embodiments, separation 502 is as wide as cut-outs 214 and 314B, as shown in FIG. 5B. As noted, some examples include removing a portion of the distal section of the anode connection member 206 such that there remains no portion or material of the cathode connection member adjacent the anode connection members 206. This is advantageous since in some examples the cathode layers can include a titanium coating, for example. A titanium coating can interfere with the performance of the anodes or can cause an electrical leakage into the weld or connection between the anodes. The present example keeps all cathode material out of the anode side 508B. In some embodiments, an electrically insulative material is inserted in separation 502. In various embodiments, separation 502 is formed by laser cutting, punching, and/or tool or machine cutting.

Figure 6:
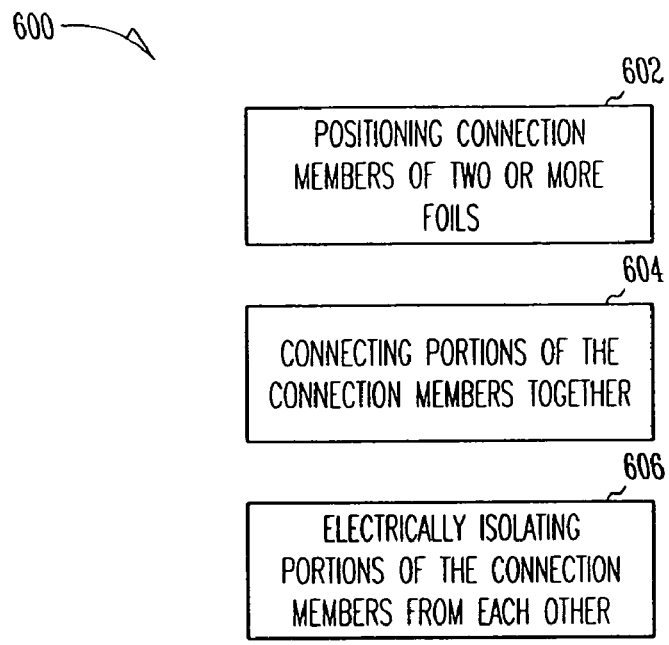
FIG. 6 is a flowchart depicting a method of interconnecting anodes and cathode foils of a capacitor according to one embodiment of the present invention.

FIG. 6 shows a flowchart depicting a method 600 for interconnecting two or more foils of a capacitor according to one embodiment of the present invention. Method 600 includes a block 602, positioning the connection members of two or more foils, a block 604, connecting the connection members, and block 606, electrically isolating portions of the connection members from each other.

In one embodiment, block 602, positioning the connection members of two or more foils, includes stacking an anode foil having a connection member having a proximal section and a distal section upon a cathode foil having a connection member having a proximal section and a distal section. The foils and connection members are positioned so that the proximal section of the anode foil connection member does not overlay the proximal section of the cathode foil connection member and the distal section of the anode foil connection member at least partially overlays the distal section of the cathode foil connection member.

In one embodiment, block 604, connecting the connection members, includes connecting the connection member of the anode foil to the connection member of the cathode foil. In one embodiment, this includes connecting the distal section of the anode connection member and the distal section of the cathode connection member at a portion of the anode connection member that overlays (or underlays) the portion of the cathode connection member. In one embodiment, connecting comprises a single, continuous connection process. For instance, a laser weld or staking process is performed which attaches all the anode and cathode foil connection members together during a single, uninterrupted process. In one embodiment, the connection is performed by edge-welding at least a portion of the distal sections of the anode foil and the cathode foil together. One embodiment includes a laser edge-welding process.

Alternatively, in some embodiments, a portion of the stack is welded during a different process or by a different method than the first process. Some embodiments include soldering, staking, swaging, and/or applying an electrically conductive adhesive.

In one embodiment, connection members 206 and 306 are laser edge-welded to each other by a process as discussed in co-pending U.S. patent application Ser. No. 09/706,518, filed on Nov. 3, 2000, the specification of which is incorporated herein by reference.

In one embodiment, block 606, electrically isolating portions of the connection members from each other, includes removing portions of the anode connection member and/or the cathode connection member. In one embodiment, the removed portion includes where the cathode connection member overlays (or underlays) a portion of the anode connection member. In one embodiment, this includes removing a portion of the distal sections of the anode connection member and the cathode connection member. In one embodiment, electrically isolating comprises punching-out a portion of the distal section of the anode foil connection member and the distal section of the cathode foil connection member. In one embodiment, electrically isolating includes laser cutting a portion of the distal section of the anode connection member and the distal section of the cathode connection member.

After being processed as discussed above in block 606, proximal sections 208 of the connection members of anodes 202 are still coupled together and proximal sections 308 of the connection members of cathodes 302 are still coupled to each other, while the anodes 202 and cathodes 302 are electrically isolated from each other. Feedthroughs or other terminal members are then used to couple the anodes and cathodes to outside circuitry.

One aspect of the present capacitor includes a system for interconnecting anode layers in a flat capacitor stack using vias. In one embodiment, vias are employed to interconnect anode layers. In one embodiment, the vias are made by inserting conductive interconnects which interconnect anode layers without contacting an intervening cathode layer.

Figure 7:
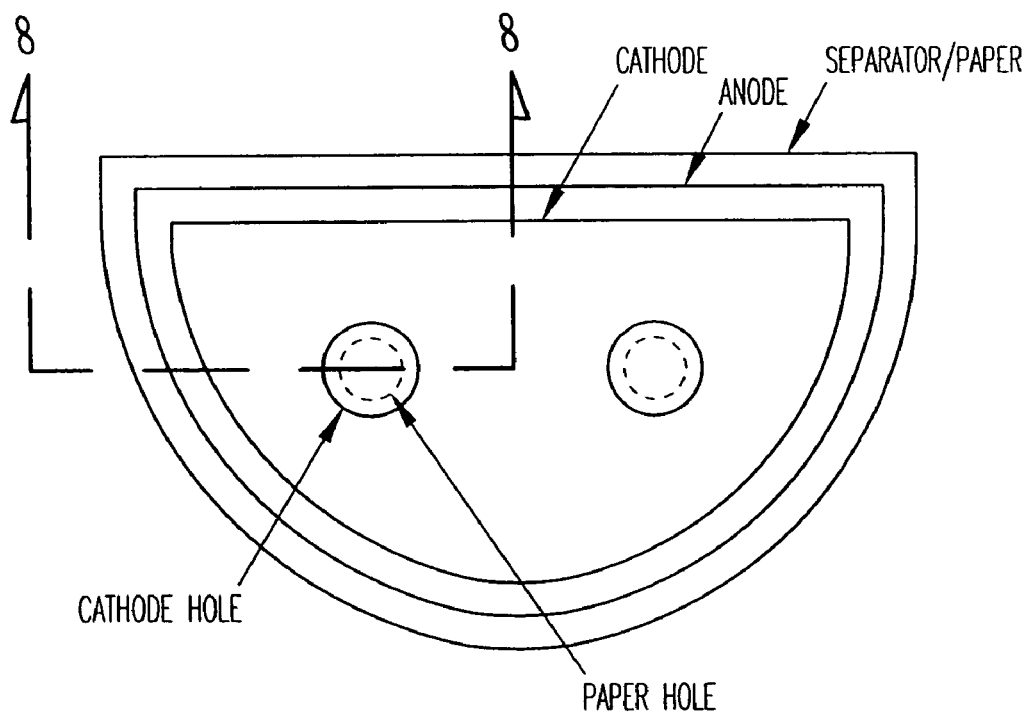
FIG. 7 shows a top view of a capacitor stack according to one embodiment.
Figure 8:
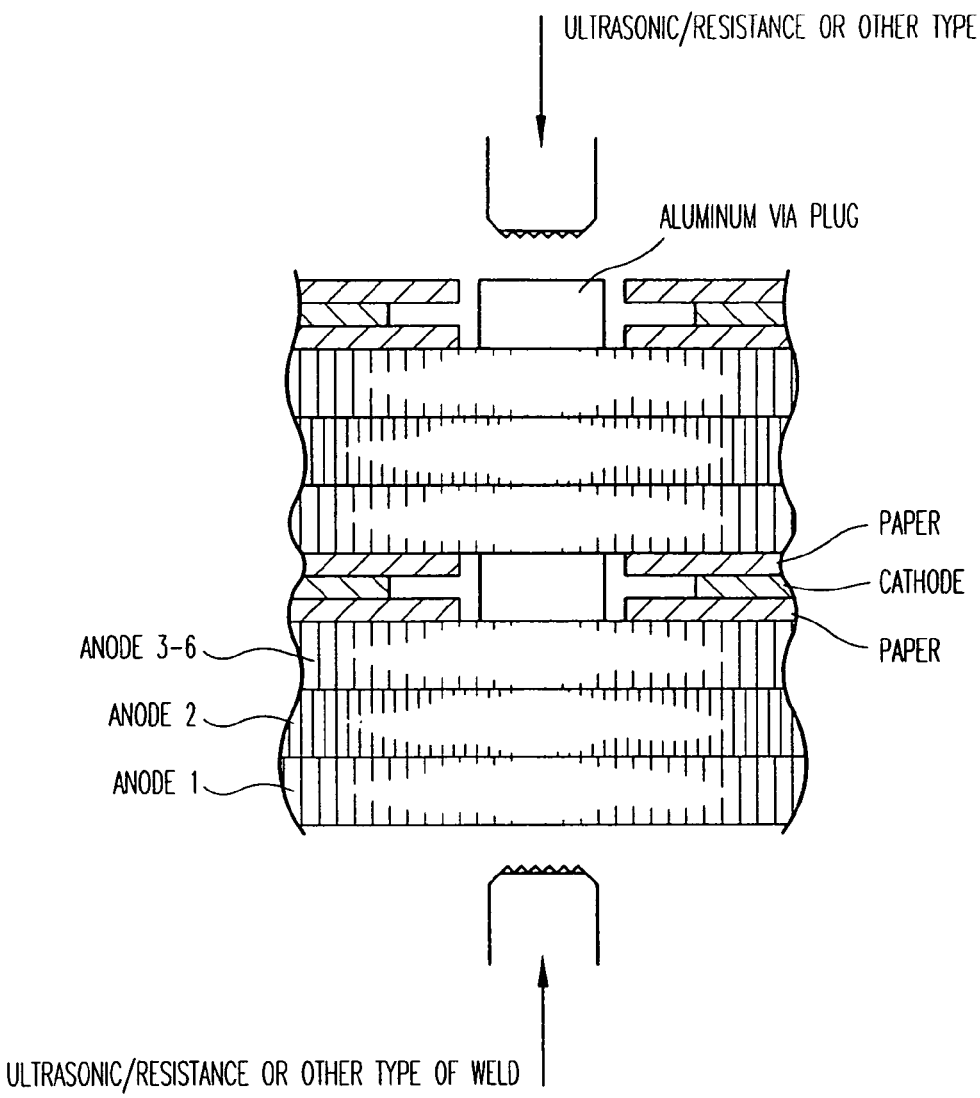
FIG. 8 shows a cross-section of a portion of FIG. 7.

For example, FIG. 7 shows a top view of a cathode and anode layer separated by separator (for example, kraft paper). The cathode layer includes one or more holes which provide ample clearance for a conductive interconnect. The x-section of FIG. 7, shown in FIG. 8, shows that the conductive interconnect will interconnect anode layers without contacting an intervening cathode layer. Thus, the cross section of the cathode hole exceeds that of the conductive interconnect to avoid shorting the cathode to the anodes. The conductive interconnect is electrically connected to the anodes by welding, such as ultrasonic, resistance or other types of welding.

Figure 9:
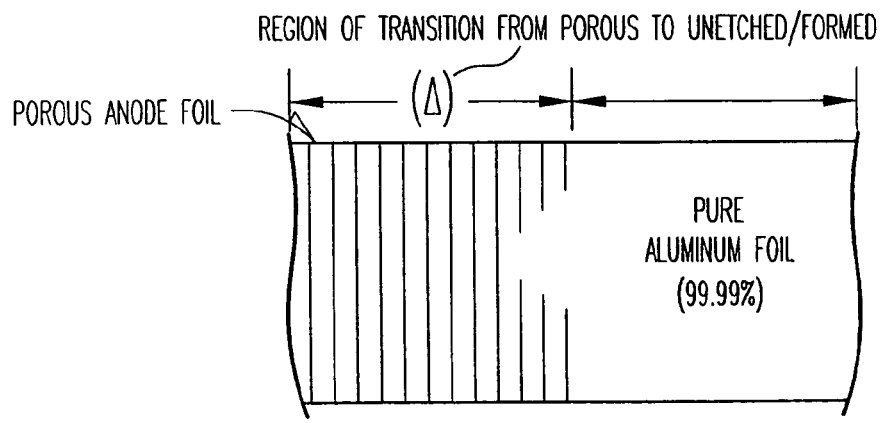
FIG. 9 shows a partially etched anode foil according to one embodiment.

One way to facilitate connections is to use a masking process for connection surfaces on the foil to ensure that the masked surfaces are not etched and/or formed. One way to avoid mechanical breakage of the foils is to use a masking technique which provides gradually non-etched portions of the foil to avoid mechanical stresses (e.g. high stress points) due to discontinuities of etching and which provides a suitable region for interconnection of the via to the foil. This is demonstrated by FIG. 9. The vertical lines show the cross-section of unmasked and masked foil portions. The figure shows that foil etching gradually diminishes over the transition from masked portion to unmasked portion. It is noted that the example shows a pure aluminum foil, but that other etchings and foils may be masked without departing from the scope of the present system.

Figure 10:
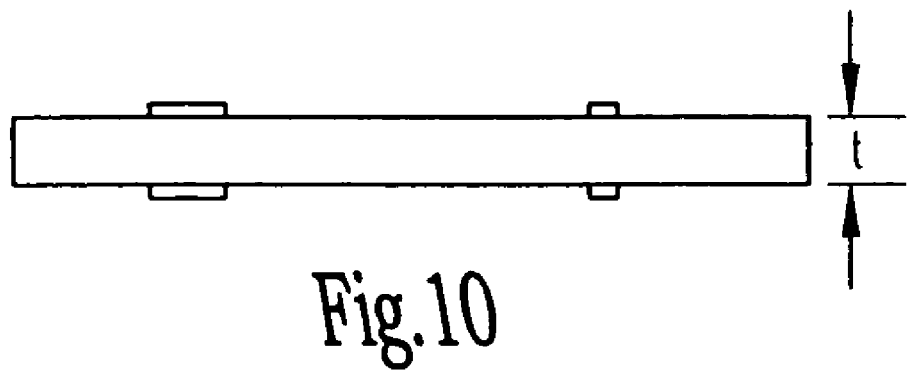
FIG. 10 shows a side view of a foil having masks according to one embodiment.
Figure 11:
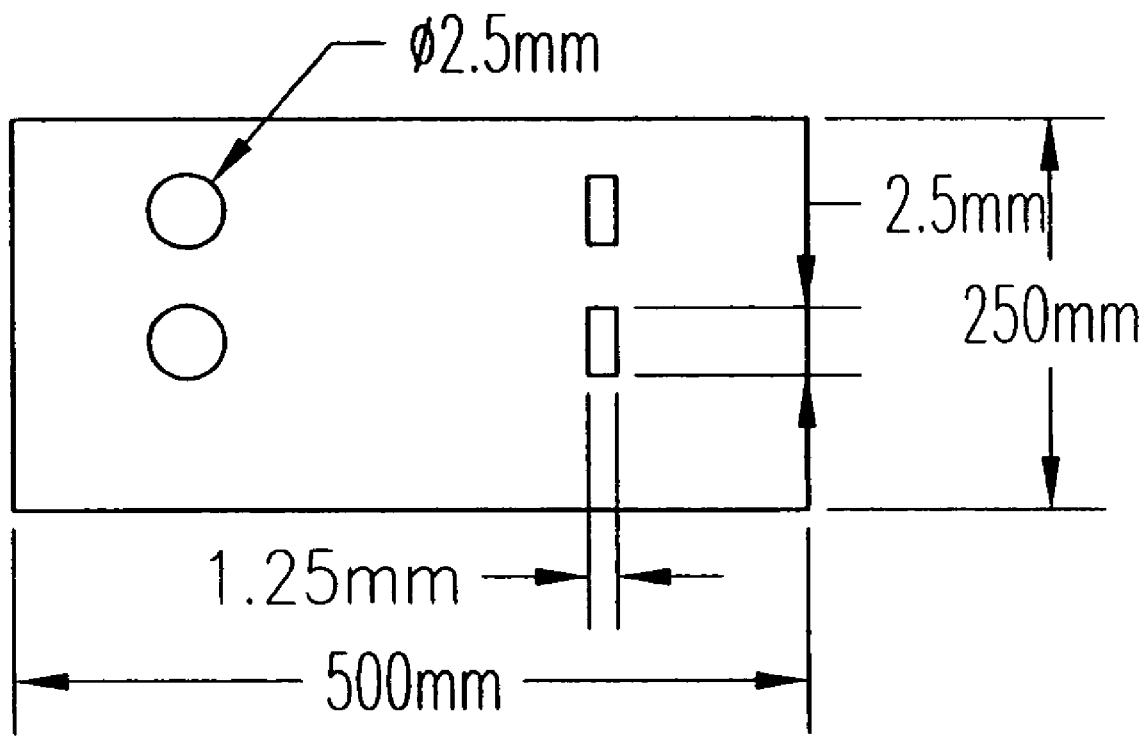
FIG. 11 show a top view of FIG. 10.

FIG. 10 shows a side view of a foil and positions of the masks for one embodiment of the present system. The top view is provided in FIG. 11. The positions, shapes and sizes of the masks may vary without departing from the present system, and the demonstrated masks are shown to illustrate the system and are not intended in an exhaustive or exclusive sense. In one embodiment, thickness t is 100 micrometers. However, it is contemplated that other thicknesses may be used without departing from the present system. For example, other thicknesses, including, but not limited to, 50-600 micrometers may be used.

The foil dimensions are shown as 500×250 millimeters, but other sized foils may be employed without departing from the scope of the present system. In one application of the present system, a master roll of foil is masked to provide d-shaped cutouts with accurately placed masks where the conductive interconnects are to contact the foil. In one application, the spacing between foils must be large enough to provide a "web" for processing the cutouts.

Figure 12:
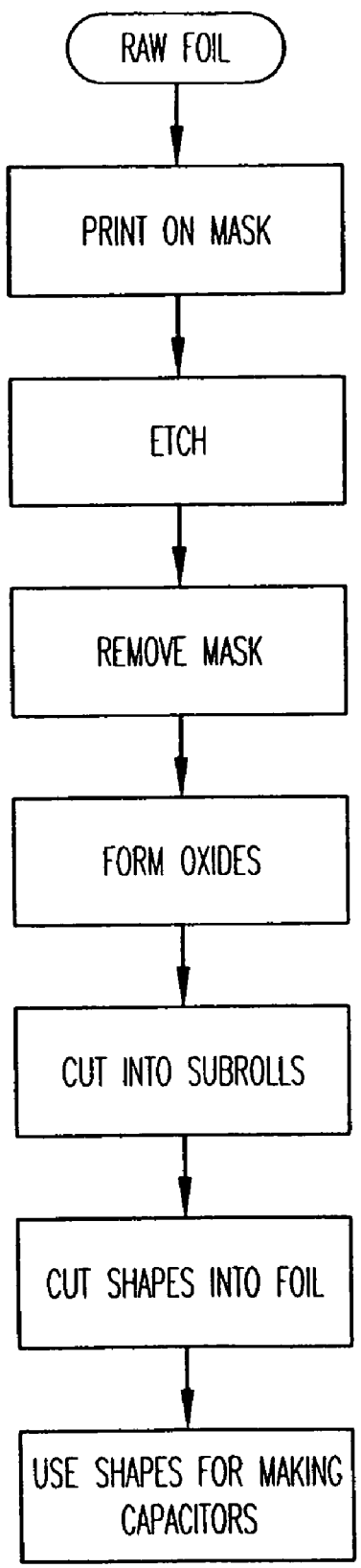
FIG. 12 shows a method according to one embodiment.

FIG. 12 shows one process for providing one embodiment of a capacitor according to some of the teachings herein. Raw foil is masked by printing the mask on the foil. The masked foil is etched and then the mask is removed. Oxides are formed on the foil and it is then cut into subrolls. The subrolls are processed by cutting shapes for the final capacitor out of the subrolls. The foil shapes are used to make the capacitors.

The cathode foils are processed to accurately place the cathode holes, which correspond to anode mask layers when overlapped. Paper separators are also cut to provide space for the conductive interconnects. In one application, the perimeter of the paper is smaller than that of the cathode to provide a nonconductive guide for the conductive interconnect. In alternate embodiments, an insulator may be used to position the conductive interconnect and to insulate against cathode contact.

It is noted that the conductive interconnects may be connected to formed or unformed portions of the anode layer.

One way to manufacture a capacitor according to the present teachings is to use a robotic assembly method, whereby anodes which are already masked, etched, and formed are stacked, followed by separator material, and then cathode material. In one assembly process, the cathodes are precision punched to provide accurately placed cathode holes. The robot can use the cathode features to accurately place the cathode relative to the anodes. A separator layer and an anode layer are also placed over the cathode using the robot. In embodiments where the conductive interconnect is a metal plug, the robot places the conductive plug accurately prior to the placement of the separator and anode layers. This process may be repeated to provide a stack of anodes of multiple layers interspersed with separator and cathode layers. The robot can also be used to perform the welding steps.

Other types of conductive interconnects may be used without departing from the present system. For example, the conductive interconnects may be made of a non-circular cross section. The conductive interconnects may be made of a suitable metal, such as aluminum. The conductive interconnects may also be made of other materials, including, but not limited to, conductive epoxy, conductive polymer (such as polyimide filled with aluminum), or fused aluminum powder. The metal used in the conductive interconnect should match the anode metal. Other anode metals/interconnect metal pairs may be used including, but not limited to, tantalum, bafnium, niobium, titanium, zirconium, or combinations of these metals.

It is understood that other connections may be performed using the teachings provided herein. For example, it is possible to create a series of interconnections between cathode layers using the teachings provided. Thus, use of the present system is not limited to anode-anode connections.

In one embodiment, the anode layers consist of a plurality of anode foils. In one application is it is possible that a single anode foil is interconnected to a triple anode foil or any multiplicity of anode foil combinations.

In one embodiment an anode layer may include a plurality of parts and/or layers. For example, the anode layer may include two different anode shapes in the same layer to provide a contoured edge. The shapes may be electrically connected to provide an equipotential surface. The use of multiple anode parts for a single layer facilitates the construction of a capacitor of virtually any form factor.

Furthermore, it is possible to weld multiple anode-cathode-anode stacks at different points for different conductive interconnects in one operation. Additionally, depending on the welding process used, several anode/cathode layers can be welded in a single operation.

Some of the benefits of the present system include, but are not limited to, the following: the electrical connection system provides mechanical stability; and alignment to the stack as the layers are being assembled; taping is not required; the assembly is ready for insertion into the capacitor case; surface area is optimized; interior alignment is facilitated using interior features to align the stack layer to layer; edge-welding and/or intra-anode staking may be eliminated; and, in some embodiments, paper gluing may be eliminated.

Exemplary Embodiment of Implantable Defibrillator

Figure 13:
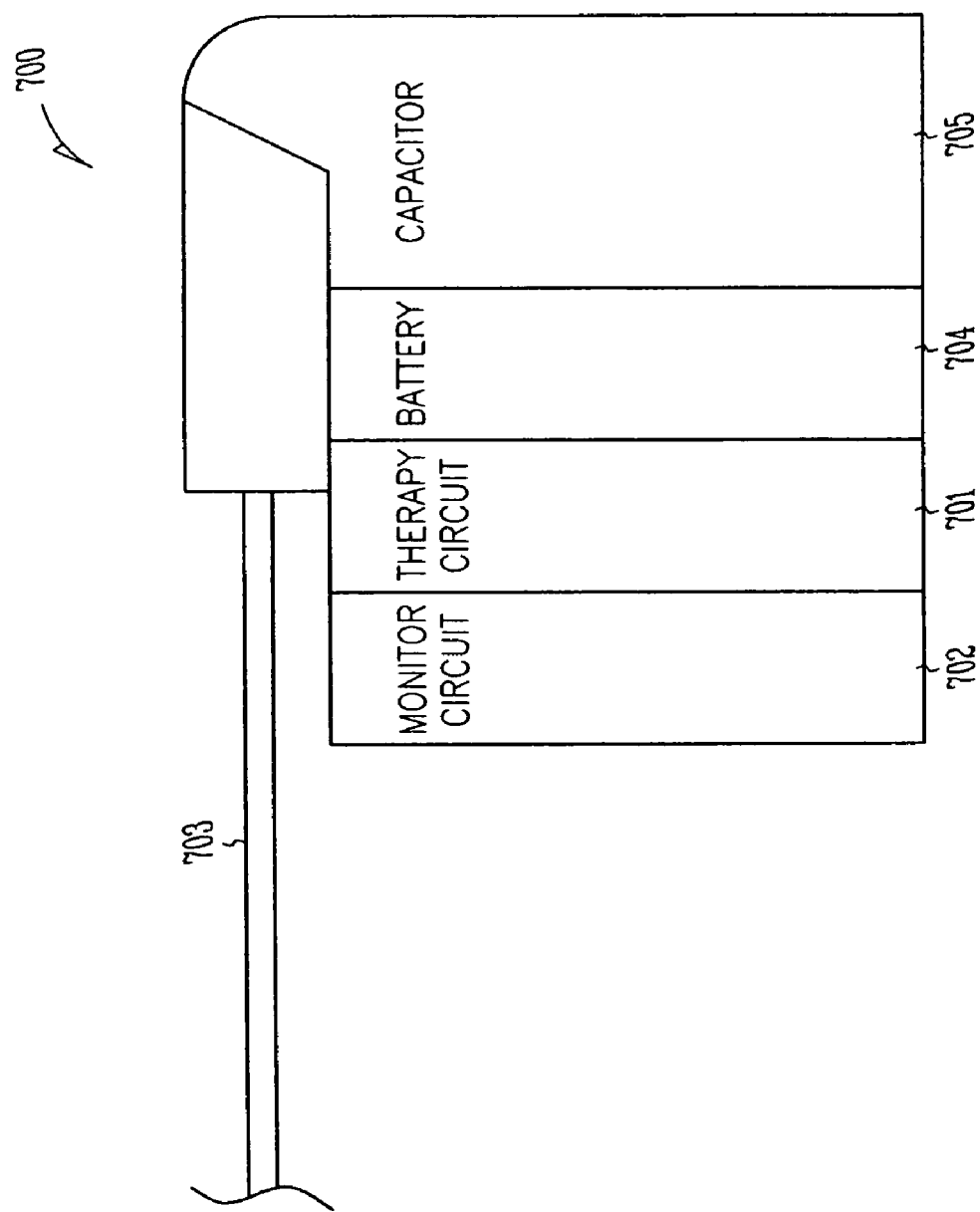
FIG. 13 is a block diagram of a generic implantable medical device including a capacitor according to one embodiment of the present invention.

FIG. 13 shows one of the many applications for capacitors incorporating one or more teachings of the present invention: an implantable heart monitor or apparatus 700. As used herein, implantable heart monitor includes any implantable device for providing therapeutic stimulus to a heart muscle. Thus, for example, the term includes pacemakers, defibrillators, cardioverters, congestive heart failure devices, and combinations and permutations thereof.

Heart monitor 700 includes a lead system 703, which after implantation electrically contact strategic portions of a patient's heart. Shown schematically are portions of monitor 700 including a monitoring circuit 702 for monitoring heart activity through one or more of the leads of lead system 703, and a therapy circuit 701 for delivering electrical energy through one or more of the leads to a heart. Monitor 700 also includes an energy storage component, which includes a battery 704 and incorporates at least one capacitor 705 having one or more of the features of the exemplary capacitors described above.

In addition to implantable heart monitor and other cardiac rhythm management devices, one or more teachings of the present invention can be incorporated into cylindrical capacitors and/or capacitors used for photographic flash equipment. Indeed, teachings of the invention are pertinent to any application where high-energy, high-voltage, or space-efficient capacitors are desirable. Moreover, one or more teachings are applicable to batteries.

CONCLUSION

In furtherance of the art, the inventors have devised connection structures and methods for interconnecting the anode foils and the cathode foils of capacitors. In one embodiment, a method includes connecting together one or more anode connection members of one or more anode foils and one or more cathode connection members of one or more cathode foils and electrically isolating the one or more anode foils from the one or more cathode foils. Among other advantages, the exemplary method reduces the number of processing steps for constructing a capacitor.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method comprising:
    positioning an anode connection member having a distal section and a proximal section and a cathode connection member having a distal section and a proximal section so that the distal section of the cathode connection member at least partially overlays the distal section of the anode connection member;
    electrically connecting the anode connection member to the cathode connection member to form a connection; and
    forming a separation in the connection between the anode connection member and the cathode connection member such that the proximal section of the anode connection member is electrically isolated from the proximal section of the cathode connection member.

2. The method of claim 1, wherein positioning further includes positioning the anode connection member and the cathode connection member so that the distal section of the cathode connection member does not overlay the entire distal section of the anode connection member.

3. The method of claim 1, wherein connecting includes connecting the distal section of the anode connection member to the distal section of the cathode connection member.

4. The method of claim 1, wherein forming a separation includes removing a portion of the distal section of the anode connection member.

5. The method of claim 1, wherein forming a separation includes removing a portion of the distal section of the anode connection member and a portion of the distal section of the cathode connection member.

6. The method of claim 1, wherein forming a separation includes removing a portion of the distal section of the anode connection member such that there remains no portion of the distal section of the cathode connection member adjacent the distal section of the anode connection member.

7. The method of claim 1, wherein positioning includes positioning the anode connection member and the cathode connection member so that the distal section of the cathode connection member overlays the entire distal section of the anode connection member.

8. The method of claim 1, wherein connecting includes connecting during a continuous connection process.

9. The method of claim 1, wherein connecting includes using an uninterrupted connecting process to connect an edge of the distal section of the anode connection member to an edge of the distal section of the cathode connection member.

10. The method of claim 1, wherein connecting includes laser welding.

11. The method of claim 1, wherein connecting includes edge-welding.

12. The method of claim 1, wherein forming a separation includes laser cutting.

13. The method of claim 1, wherein forming a separation includes punching.

* * * * *